(12) United States Patent
Takami (10) Patent No.: US 6,545,523 B1
(45) Date of Patent: Apr. 8, 2003

(54) AIR DELIVERY UNIT FOR ENDOSCOPE INCLUDING PRESSURE DETECTING APPARATUS

(75) Inventor: Satoshi Takami, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/455,933

(22) Filed: Dec. 7, 1999

(30) Foreign Application Priority Data

Dec. 11, 1998 (JP) .......................................... 10-352626

(51) Int. Cl.[7] ............................................... H03K 17/14
(52) U.S. Cl. ......................................... 327/378; 73/708
(58) Field of Search .............................. 327/513, 517, 327/378; 73/708; 600/560

(56) References Cited

U.S. PATENT DOCUMENTS

| | | | | |
|---|---|---|---|---|
| 4,362,060 A | * | 12/1982 | Okayama et al. | 73/708 |
| 4,463,274 A | * | 7/1984 | Swartz | 327/513 |
| 5,377,688 A | | 1/1995 | Aviv et al. | 128/747 |
| 5,515,860 A | | 5/1996 | Aviv et al. | 128/747 |

* cited by examiner

Primary Examiner—Kenneth B. Wells (57) ABSTRACT

An air delivery unit for an endoscope includes a pressure-sensor, a voltage descent processor, an amplifier, and an electric power supplier. A closed-space is formed in the air delivery unit. The air delivery unit adjusts a pressure in the closed-space by measuring the pressure and then discharging air in the closed-space.

9 Claims, 8 Drawing Sheets

AIR DELIVERY UNIT FOR ENDOSCOPE INCLUDING PRESSURE DETECTING APPARATUS

BACKGROUND OF THE INVENTION

1. Field of the Invention

This invention relates to an air delivery unit for an endoscope, which delivers air into an organ, such as a stomach.

2. Description of the Related Art

Conventionally, an air delivery unit for an endoscope, which delivers air into a body-cavity of a patient, is known. In the air delivery unit, a compressor for compressing the air and a valve for regulating an amount of the discharge of the air are provided, and further a closed-space, in which the air is stored, is formed.

A pressure in the closed-space is adjusted by operating the compressor and the valve such that the pressure in the closed-space equals a setting pressure set by an operator. After the pressure in the closed-space is adjusted, the air in the closed-space is discharged by opening and shutting the valve. The discharged air is delivered into the organ via a video-scope or an optical fiber-scope, and thus a condition of a diseased portion is confirmed.

In order to measure a pressure value in the closed-space during an adjustment of the pressure, a pressure-sensor and an electric circuit including an amplifier and a comparator are provided in the air delivery unit. When the pressure in the closed-space is detected by the pressure-sensor, a voltage, corresponding to the pressure value in the closed-space, is fed from the pressure-sensor to the amplifier. In the amplifier, the voltage fed from the pressure-sensor is amplified. The amplified voltage is fed to the comparator as an output-voltage and then compared with a voltage corresponding to the setting pressure. A power-supply voltage is applied to the pressure-sensor, the amplifier and the comparator via a converter, respectively, and thus the pressure-sensor, the amplifier and the comparator act.

In general, a maximum output-voltage of the output-voltage never exceeds the power-supply voltage of the amplifier. Herein, an input-voltage, corresponding to the maximum output-voltage, is referred to as a limitation input-voltage. When a voltage exceeding the limitation input-voltage is input from the pressure-sensor to the amplifier, a voltage amplified by a predetermined voltage-gain can not be output to the comparator. On the other hand, as the pressure-sensor is designed such that the pressure in the closed-space is measured as precisely as possible, the range of the input-voltage value, in short, the range of the voltage output from the pressure-sensor is sufficiently broad. Therefore, an input-voltage, exceeding the limitation voltage, is occasionally input to the amplifier. When the input-voltage exceeding the limitation voltage is input to the amplifier, a voltage corresponding to the pressure value measured by the pressure-sensor is not output to the comparator, so that pressure in the closed-space can not be adjusted properly.

To solve this problem, conventionally, the power-supply voltage of the amplifier is lifted to lift a value of the limitation input-value. However, as the power-supply voltage of the amplifier is higher than that of the comparator, an operation of the electric circuit becomes unstable, namely, the reliability of the circuit is degraded. Further, as plural converters are required to be provided in the air delivery unit, the number of components increases.

SUMMARY OF THE INVENTION

Therefore, an object of the present invention is to provide an air delivery unit for an endoscope, in which the pressure value in the closed-space can be measured precisely without complicating the construction of the electric circuit.

An air delivery unit for an endoscope comprises a pressure-sensor, a voltage descent processor, an amplifier, an electric power supplier. Further, in the air delivery unit a closed-space is formed, the air delivery unit adjusting a pressure in the closed-space by measuring the pressure and then discharging air in the closed-space. The pressure-sensor outputs a pressure-voltage corresponding to a value of the pressure in said closed-space. The voltage descent processor lowers the pressure-voltage and outputs a lowered pressure-voltage. The amplifier amplifies the lowered pressure-voltage generated by the voltage-descent processor and then outputs an amplified pressure-voltage. The electric power supplier applies a power-supply voltage to the pressure-sensor and the amplifier. The voltage descent processor lowers the pressure-voltage such that a linear relationship between the pressure-voltage output from the pressure-sensor and the amplified pressure-voltage output from the amplifier is maintained.

BRIEF DESCRIPTION OF THE DRAWINGS

The present invention will be better understood from the description of the preferred embodiment of the invention set forth below together with the accompanying drawings, in which.

DESCRIPTION OF THE PREFERRED EMBODIMENT

Hereinafter, the preferred embodiment of the present invention is described with reference to the attached drawings.

Figure 1:
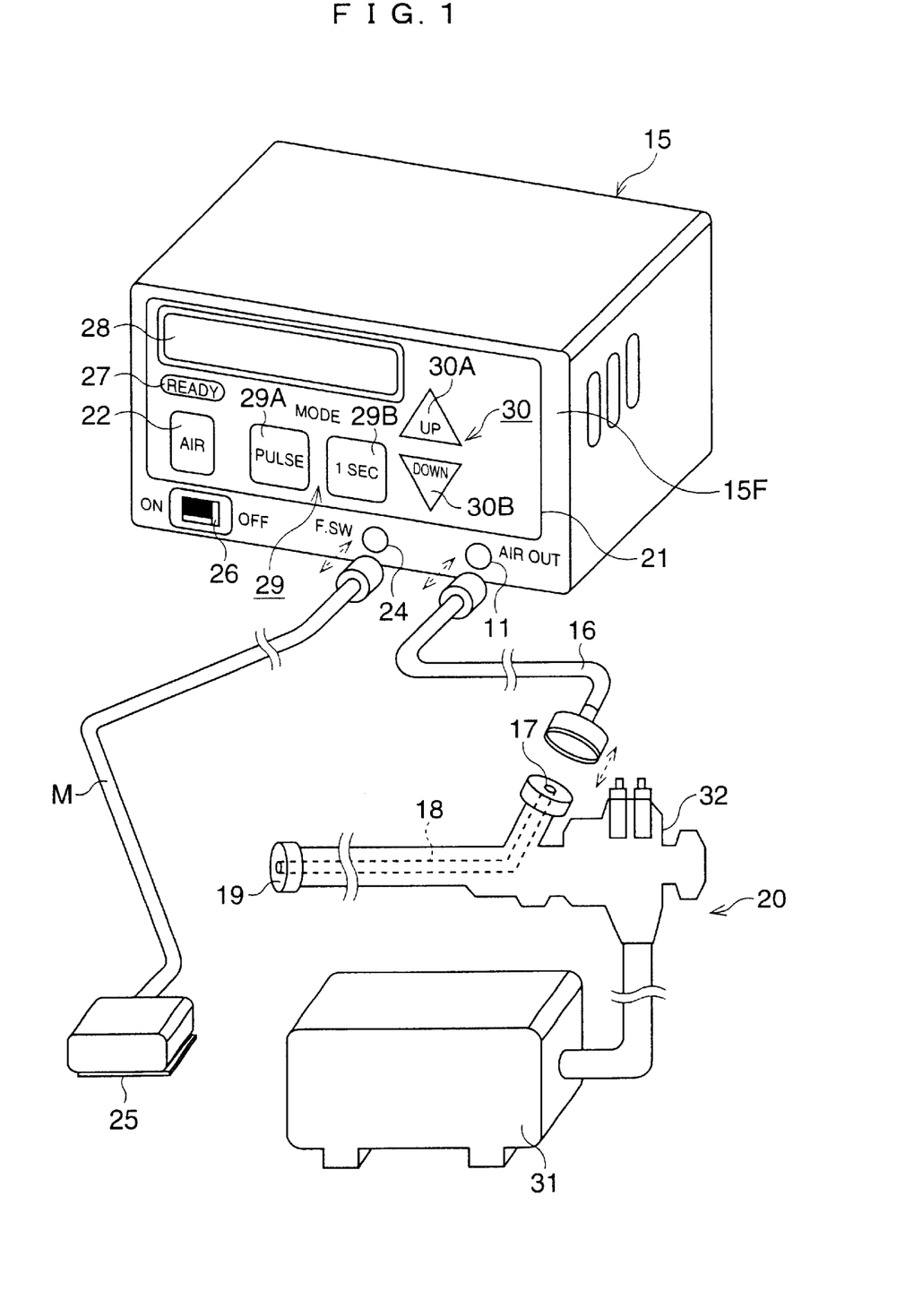
FIG. 1 is a perspective view showing an air delivery unit for an endoscope of the present invention.

FIG. 1 is a perspective view showing an air delivery unit for an endoscope of the present invention. This unit is used when an inspection of a diseased portion in an organ, such as a stomach, is performed. Note that, in the air delivery unit, as described later, a closed-space is formed.

In the air delivery unit 15, an operation panel 21, a power switch 26, outlet 11, and a jack 24 are disposed on a front surface 15F. On the operation panel 21, a discharge-mode switch 29 for setting a discharge-mode, a pressure switch 30 for setting a pressure in the closed-space and a discharge switch 22 for carrying out a discharge of air in the closed-space are arranged.

The discharge-mode switch 29 is composed of a pulse switch 29A and a continuity switch 29B. The pulse switch 29A is a switch for discharging one pulse worth of air in the closed-space, in short, a puff of air. The continuity switch 29B is a switch for continuously discharging the air in the closed-space for a predetermined period. In this embodiment, the predetermined period is 1 sec. Either the pulse switch 29A or the continuity switch 29B is selected by an operator.

The pressure switch 30 is composed of an up-switch 30A and down-switch 30B. When the up-switch 30A is operated, the pressure in the closed-space is increased. Inversely, when the down-switch 30B is operated, the pressure in the closed-space is decreased.

An indicator light 27, disposed above the discharge switch 22, indicates a completion of preparation for a discharge of the air. The discharge switch 22 is provided for carrying out a discharge of the air in the closed-space. When the discharge switch 22 is operated by the operator, the air in the closed-space is discharged through the outlet 11.

A display 28 is disposed above the discharge-mode switch 29 and the pressure switch 30, on the operation panel 21. When the pressure switch 30 is operated, a pressure value of the closed-space, set by the operator, is displayed on the display 28. A foot switch 25 is connected to the jack 24 via a cord M, whereby a remote control of the discharge of the air can be performed.

A tube 16 is connected to the outlet 11 such that the air in the closed-space is delivered to an electronic endoscope 20. The electronic endoscope 20 comprises a flexible video-scope 32 having an image sensor (not shown) and a video-processor 31. In the video-scope 32, a forceps tube 18 is provided therethrough and an end of the tube 16 is detachably connected to a forceps-inlet 17 provided at a proximal end of the video-scope 32. When a medical inspection is performed, the video-scope 32 is inserted into an organ. Then, the air discharged from the outlet 11 is delivered into the video-scope 32 via the tube 16, and the air is discharged from a forceps-outlet 19 provided at a distal end of the video-scope 32.

The video-scope 32 is connected to the video-processor 31, and a TV monitor (not shown) is also connected to the video-processor 31. The object image is formed on the image sensor provided at the distal end of the video-scope 32, and is then converted into image signals by photoelectric conversion. The image signals are fed to the video-processor 31, and thus, the object image is displayed on the monitor.

Figure 2:
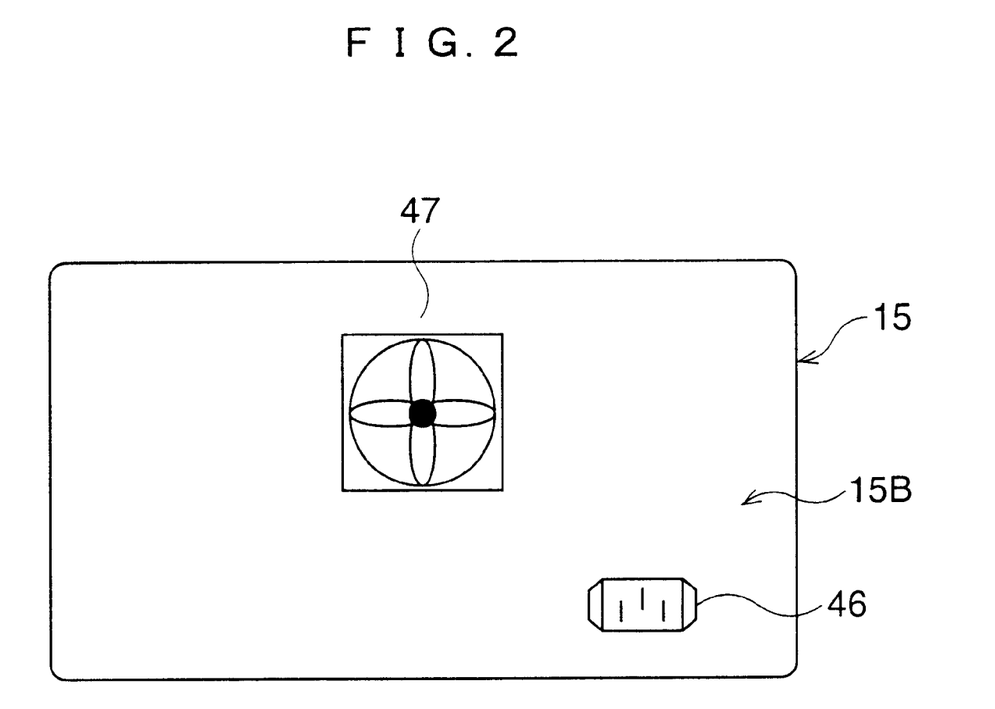
FIG. 2 is a view showing a back surface of the air delivery unit.

FIG. 2 is a view showing a back surface of the air delivery unit 15. On the back surface 15B, a fan 47 and an AC inlet 46 are provided. The fan 47 sends outer air into the air delivery unit 15 to cool the air in the closed-space. Electric power is supplied to the air delivery unit 15 through the inlet 46.

Figure 3:
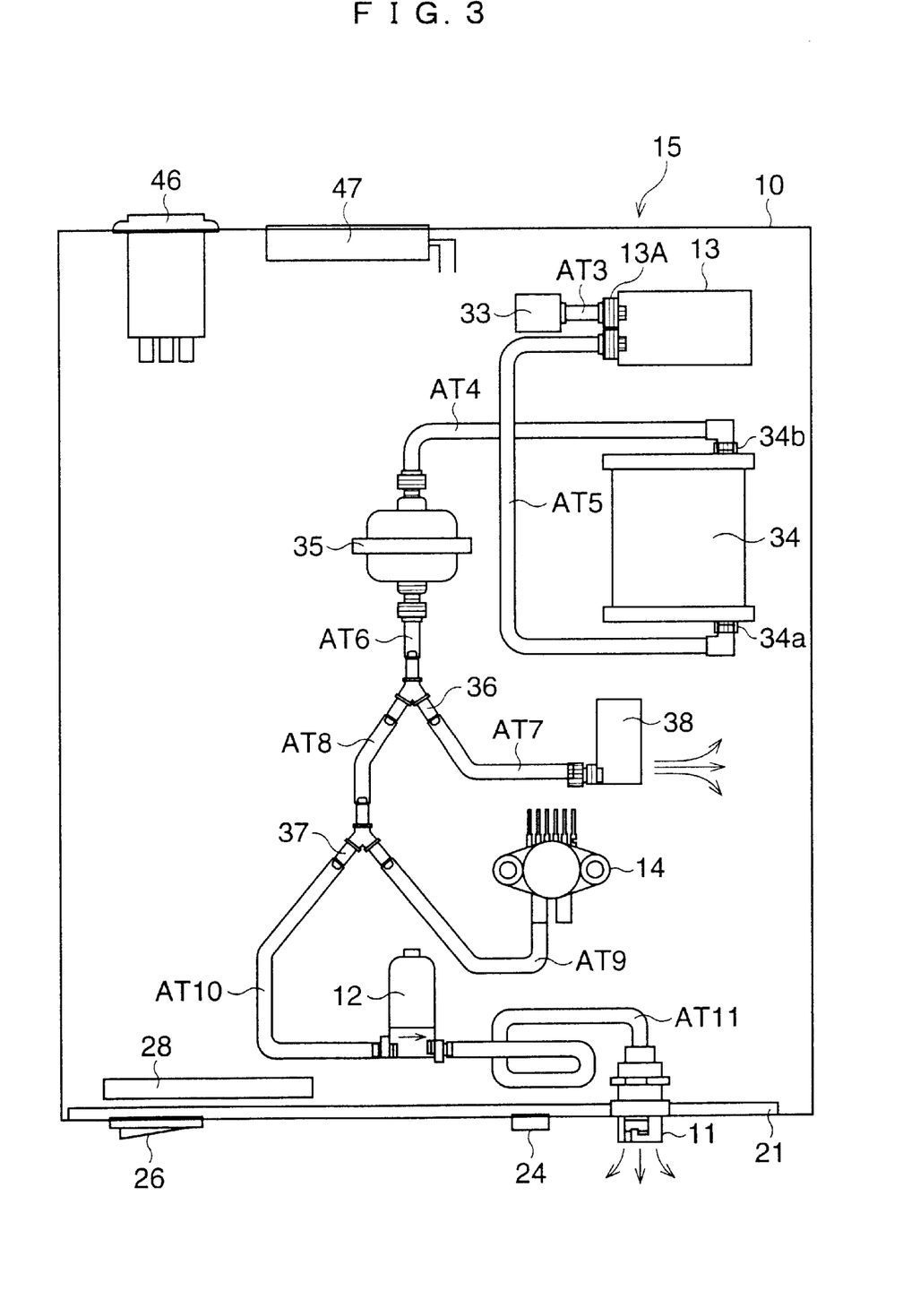
FIG. 3 is a view showing structural elements in the air delivery unit.

FIG. 3 is a view showing an arrangement of main structural elements provided in the air delivery unit 15. The AC inlet 46, the power switch 26, and the operation panel 21 including the display 28 are respectively disposed on housing 10 of the air delivery unit 15.

In the housing 10, the closed-space is formed by linking a compressor 13, an air-tube AT5, an air-tank 34, an air-tube AT4, an air-filter 35, an air-tube AT6, a connector 36, an air-tube AT7, a pressure-control valve 38, an air-tube AT8, a connector 37, an air-tube AT9, a pressure-sensor 14, an air-tube AT10, and a discharge valve 12 together. The air in the closed-space is not discharged except when the pressure-control valve 38 or the discharge valve 12 opens. The pressure-control valve 38 is closed except when an adjustment of the pressure in the closed-space is performed. Similarly, the discharge valve 12 is closed except when the air in the closed-space is discharged.

A silencer 33, which is provided for suppressing noise generated from the compressor 13, is connected to the compressor 13 via an inlet 13A. When the compressor 13 operates, outside air is inhaled into the compressor 13, that is, the closed-space, via the silencer 33 and the air-tube AT3. At this time, the inhaled air is compressed. Thus, the pressure in the closed-space is enhanced. The compressor 13 is connected to the air-tank 34 through the air-tube AT5.

The air-tank 34 is provided to enlarge the volume of the closed-space. The volume of the air-tank 34 is larger than the total volume of the air-tubes AT4 to AT10. The air-tank 34 has an inlet 34a, to which the air-tube AT5 is connected, and an outlet 34b, to which the air-tube AT4 is connected. The air filter 35, to which the air-tank 34 is connected through he air-tube AT4, is provided for removing dust from the closed-space.

The closed-space forks at the connector 36, and the air-tube AT7 is extended toward the pressure-control valve 38. The pressure-control valve 38 is provided for adjusting the pressure in the closed-space. Further, the closed-space forks at the connector 37 and the air-tube AT9 is extended toward the pressure-sensor 14. The pressure-sensor 14 is provided for measuring the pressure in the closed-space.

When the pressure switch 30 (shown in FIG. 1) is operated, the pressure-control valve 38 opens or the compressor 13 is driven, on the basis of the pressure measured by the pressure-sensor 14. Namely, the pressure in the closed-space is adjusted so as to equal a setting pressure, set by the operation of the pressure switch 30. For example, when the pressure in the closed-space is low compared with the setting pressure, the compressor 13 is driven to enhance the pressure, while the pressure-control valve 38 remains closed. On the other hand, when the pressure in the closed-space is high compared with the setting pressure, the pressure-control valve 38 opens to emit the air in the closed-space, while the compressor does not act. When the pressure in the closed-space equals the setting pressure, the pressure-control valve 38 shuts and the compressor 13 stops.

When the discharge switch 22 or the foot switch 25 is operated after the pressure in the closed-space is adjusted, the discharge valve 12 opens, so that the air in the closed-space is discharged from the outlet 11 via the air-tube AT11. Note that, a timing of an open-close of the discharge valve 12 depends on the discharge-mode. Namely, when the pulse switch 29A is selected, the discharge valve 12 opens and closes such that a puff of air is discharged. On the other hand, when the continuity switch 29B is selected, the discharge valve opens for 1 sec.

Figure 4:
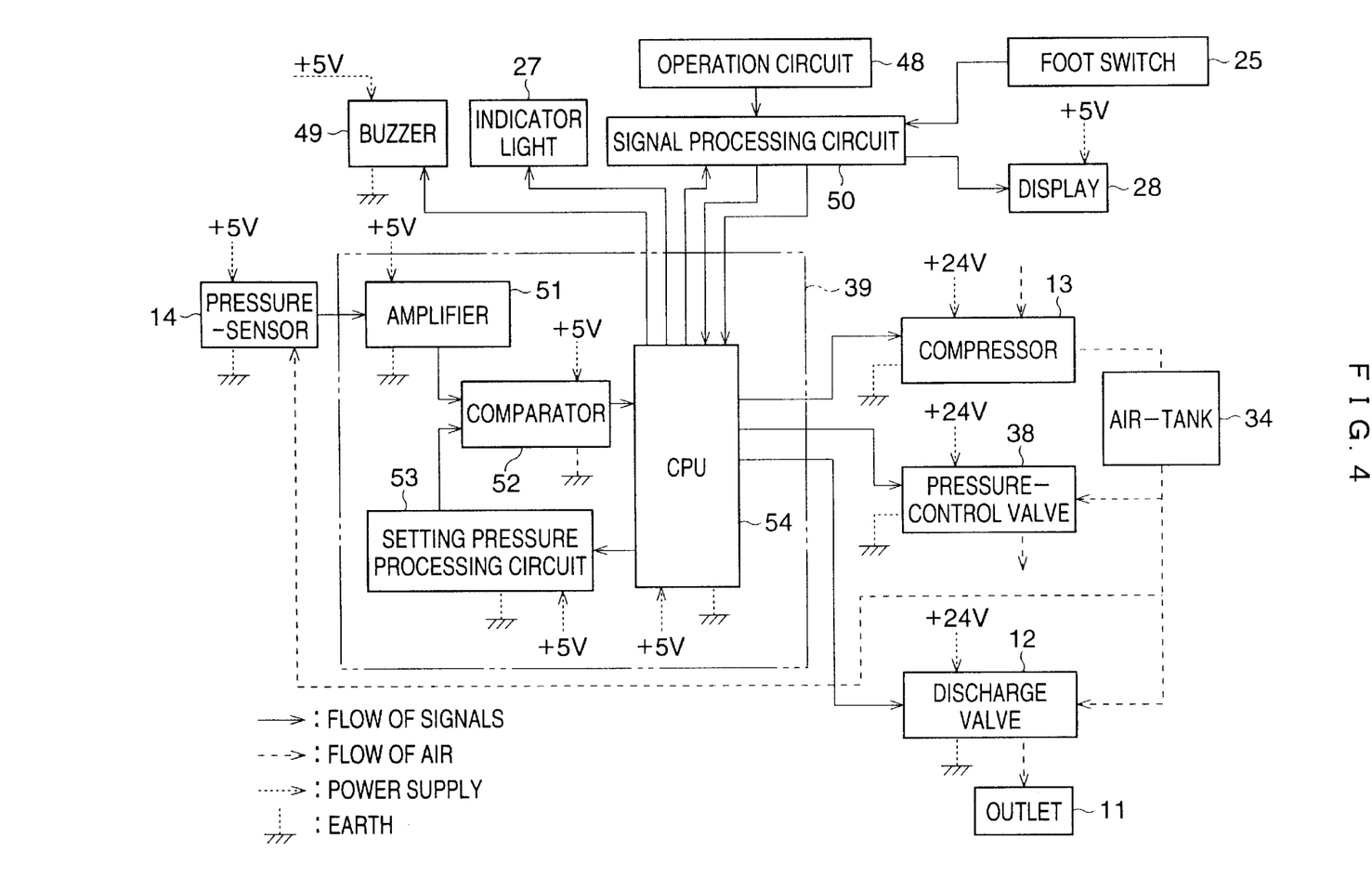
FIG. 4 is a block diagram of the air delivery unit.

FIG. 4 is a block diagram of the air delivery unit 15. A control system circuit 39 comprises an amplifier 51, a comparator 52, a setting pressure processing circuit 53, and a CPU 54. The control system circuit 39 controls the air delivery unit 15 as a whole. At the CPU 54, control-signals are output to the compressor 13, the discharge valve 12, the pressure-control valve 38, and a buzzer 49.

In an operation circuit 48, operation-signals are generated when one of the discharge switch 22, the pressure switch 30, and the discharge-mode switch 29 is operated. The operation-signals, output from the operation circuit 48 or the foot switch 25, are subjected to various processes in a signal processing circuit 50, and then fed to the CPU 54. A setting pressure signal, corresponding to the setting pressure, is fed from the CPU 54 to the display 28 via the signal processing circuit 50. Thus, the value of the setting pressure is displayed on the display 28.

A pressure signal (voltage), corresponding to a pressure value in the closed-space, is fed from the pressure-sensor 14 to the amplifier 51. In the pressure amplifier 51, the pressure signal is amplified and then is fed to the comparator 52. On the other hand, the setting pressure signal is input to the setting pressure processing circuit 53 via the CPU 54.

In the comparator 52, the pressure signal output from the amplifier 51 is compared with the setting pressure signal output from the setting pressure processing circuit 53. Namely, the pressure in the closed-space at the present is compared with the setting pressure. Then, a signal, corresponding to the difference between the pressure and the setting pressure, is fed to the CPU 54. In the CPU 54, the control-signal is fed to the pressure-control valve 38 or the compressor 13 on the basis of the signal from the comparator 52, and thus the compressor 13 or the pressure-control valve 38 is driven.

Note that, to prevent a hunting-situation, in which the compressor 13 and the pressure-control valve 38 act for a long time, from occurring, the pressure-control valve 38 and the compressor 13 are not driven when the difference between the pressure signal and the setting pressure signal is within a predetermined range.

In the buzzer 49, a buzzer, associated with the operation of the switches, sounds. The indicator light 27 is turned ON when the preparation for the discharge of the air is finished.

Figure 5:
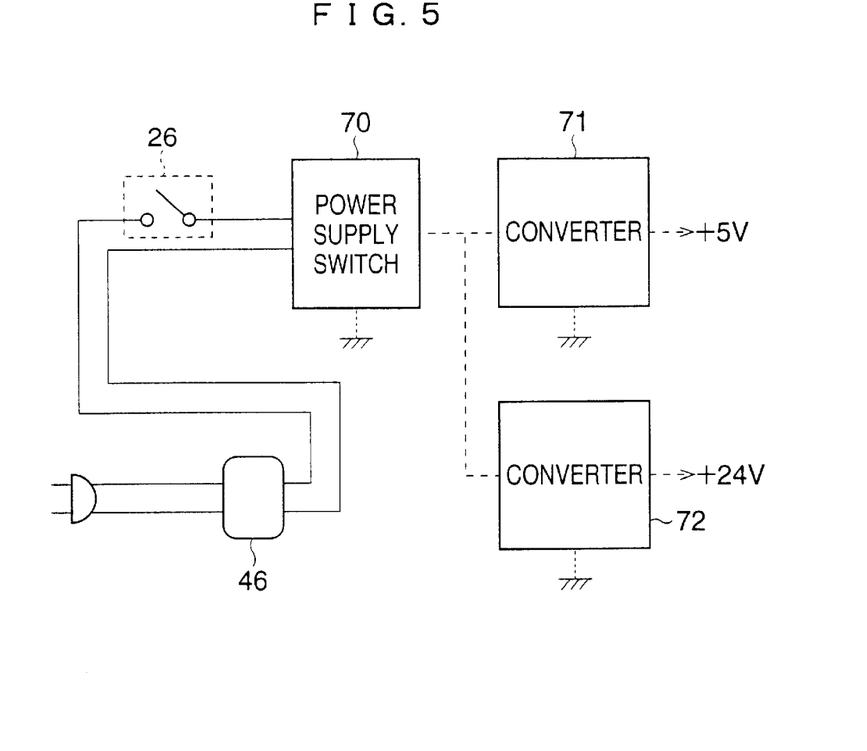
FIG. 5 is a view partially showing a power-supply circuit.

FIG. 5 is a block diagram showing the power supply circuit.

The electric power is supplied to components, in which an electric circuit is provided, such as pressure-sensor 14, through AC inlet 46, power switch 26, and power-supply switch 70.

A voltage, output from the power-supply switch 70, is converted into a DC voltage of +5 Volt in a converter 71, so that the power-supply voltage of +5 Volt is applied to the pressure-sensor 14, the amplifier 51, the comparator 52, the setting pressure processor 53, the CPU 54 and so on (See FIG. 4). Further, a voltage, output from the power-supply switch 70, is converted into a voltage of +24 Volt in a converter 72, so that the power-supply voltage of +24 Volt is, as shown in FIG. 4, applied to the compressor 13, pressure-control valve 38 and discharge valve 12.

Figure 6:
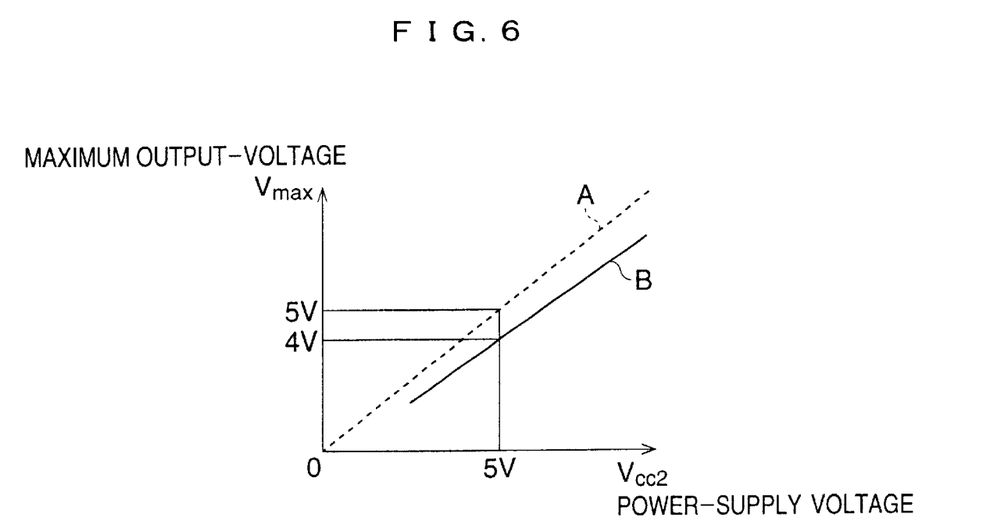
FIG. 6 is a view showing operational characteristics of an amplifier.
Figure 7:
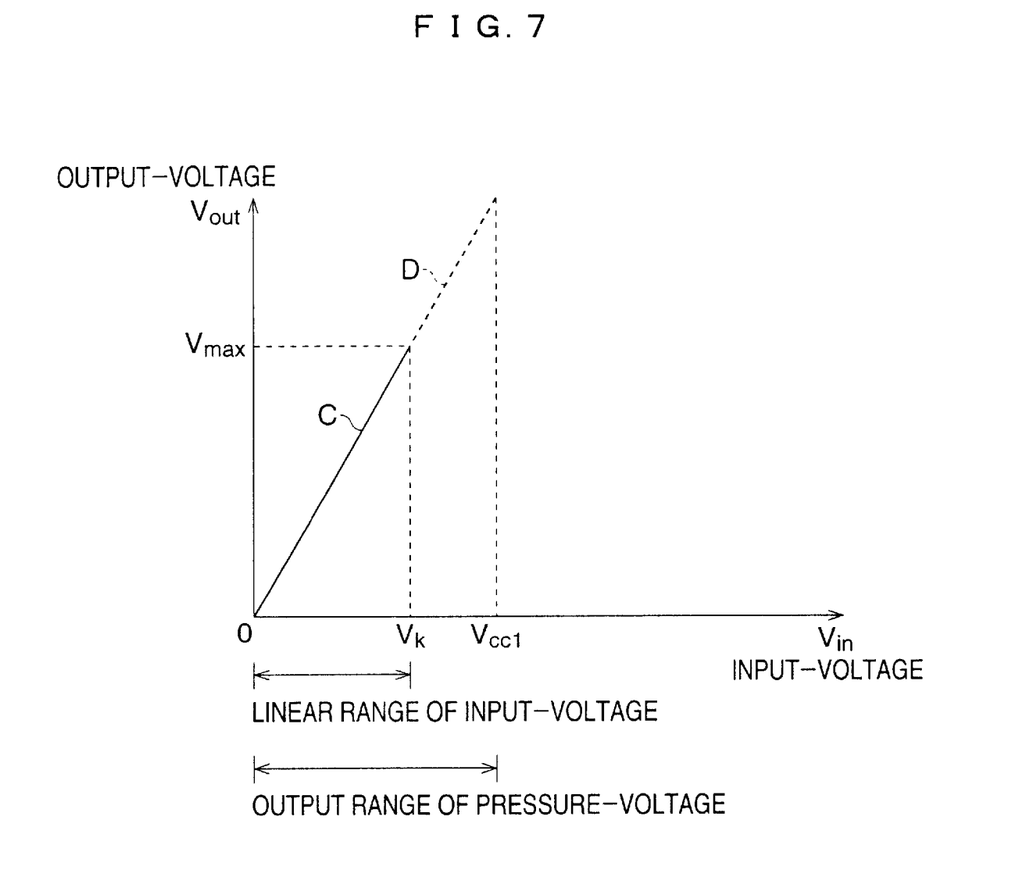
FIG. 7 is a view showing further operational characteristics of the amplifier.

FIGS. 6 and 7 are views showing operational characteristics of the amplifier 51. FIG. 6 is a view showing a relationship between a power-supply voltage $V_{cc2}$ of the amplifier 51 and a maximum output-voltage $V_{max}$ indicating a limitation of an output-voltage of the amplifier 51.

Ideally, the maximum output-voltage $V_{max}$ is equal to the power-supply voltage $V_{cc2}$ (See a broken line A). However, in fact, the maximum output-voltage $V_{max}$ is less than the power-supply voltage $V_{cc2}$ because of a characteristic of a circuit incorporated in the amplifier 51. A solid line B indicates an actual relationship between the maximum output-voltage $V_{max}$ and the power-supply voltage $V_{cc2}$. For example, when the power-supply voltage $V_{cc2}$ is 5.0 Volt, the maximum output-voltage $V_{max}$ is actually 4.0 Volt.

FIG. 7 is a view showing a relationship between an input-voltage $V_{in}$ and an output-voltage $V_{out}$ in the amplifier 51. A vertical axis shows the output-voltage $V_{out}$, and a horizontal axis shows the input-voltage $V_{in}$.

The output-voltage $V_{out}$ is given by:

$$V_{out}=V_{in} \times N \quad (1)$$

Notice that N is a voltage-gain in the amplifier 51.

As shown in FIG. 6, the maximum output-voltage $V_{max}$ is less than the power-supply voltage $V_{cc2}$. Therefore, a range of the output-voltage $V_{out}$ is as follows:

$$0 \leq V_{out} < V_{max} \leq V_{cc2} \quad (2)$$

Herein, an input-voltage $V_{in}$ corresponding to the maximum output-voltage $V_{max}$ is denoted by a limitation input-voltage $V_k$. The limitation input-voltage $V_k$ is obtained by using Equation (1) as follows:

$$V_k = V_{max}/N \quad (3)$$

In a range of the input-voltage $V_{in}$ ($0 \leq V_{in} \leq V_k$), the output-voltage $V_{out}$ is obtained by Equation (1), as shown in a solid line C. Namely, the output-voltage $V_{out}$ has a linear relation to the input-voltage $V_{in}$. Herein, the range of the input-voltage $V_{in}$ corresponding to the solid line C is denoted by a linear range of an input-voltage $V_{in}$. If an input-voltage $V_{in}$ exceeding the limitation input-voltage $V_k$ is input to the amplifier 51, an output-voltage $V_{out}$ obtained by Equation (1) is not output to the comparator 52 (shown in FIG. 4) but a voltage approximately equal to the limitation output-voltage $V_{max}$ is output to the comparator 52. Therefore, a voltage value, corresponding to the pressure value in the closed-space, can not be measured.

On the other hand, as an accuracy of the pressure-sensor 14 is improved to measure the pressure in the closed-space precisely, an output range of a pressure-voltage, output from the pressure-sensor 14 to the amplifier 51, is relatively broad compared with that of the amplifier 51. In fact, a maximum pressure-voltage is equal to a power-supply voltage $V_{cc1}$ of the pressure-sensor 14, unlike the amplifier 51. The output range of the pressure-voltage $V_p$ is as follows:

$$0 \leq V_p \leq V_{cc1} \quad (4)$$

When the power-supply voltage $V_{cc1}$ of the pressure-sensor 14 is equal to the power-supply voltage $V_{cc2}$ of the amplifier 51, the power-supply voltage $V_{cc1}$ exceeds the limitation input-voltage $V_k$, as shown in following formula:

$$V_k = V_{max}/N < V_{cc2}/N = V_{cc1}/N \leq V_{cc1} \therefore V_k < V_{cc1} \quad (5)$$

This formula is based on Equations (2), (3). Note that, the voltage-gain N is equal to or more than 1.

Therefore, when the power-supply voltage $V_{cc1}$ of the pressure-sensor 14 is equal to the power-supply voltage $V_{cc2}$ of the amplifier 51, the output range of the pressure-voltage $V_p$ exceeds the linear range of the input-voltage $V_{in}$, as shown in FIG. 7.

For example, when both the power-supply voltage $V_{cc1}$ and the power-supply voltage $V_{cc2}$ are 5.0 Volt, the limitation input-voltage $V_k$ is:

$$V_k = V_{max}/N = 4.0/1.5 = 2.67 \quad (6)$$

Therefore, when the pressure-voltage $V_p$, equal to the power-supply voltage $V_{cc1}$ (=5.0 Volt), is output from the image sensor 14 to the amplifier 51, the output-voltage $V_{out}$ is not obtained by Equation (1), as the input-voltage $V_{in}$ (=5.0 Volt) is more than the limitation voltage $V_k$ (=2.67 Volt). Namely, precise voltage corresponding to the pressure value in the closed-space can not be fed to the comparator 52.

If the power-supply voltage $V_{cc2}$ is, as conventionally applied for measuring the pressure, higher than the power-supply voltage $V_{cc1}$ (for example, the power-supply $V_{cc2}$ of 12.0 Volt), the linear range of the input-voltage $V_{in}$ exceeds the output range of the pressure-voltage $V_p$. Namely, as shown in a broken line D, the output voltage $V_{out}$ can be obtained by Equation (1).

However, in this case, the power-supply voltage of the other structural elements provided in the system control circuit 39 (shown in FIG. 4), especially the comparator 52, is less than the power-supply voltage $V_{cc2}$. Thus, the operation of the electric circuit becomes unstable as an overvoltage is occasionally applied to the electric circuit.

Accordingly, in this embodiment, a circuit for lowering the pressure-voltage $V_p$ is provided.

Figure 8:
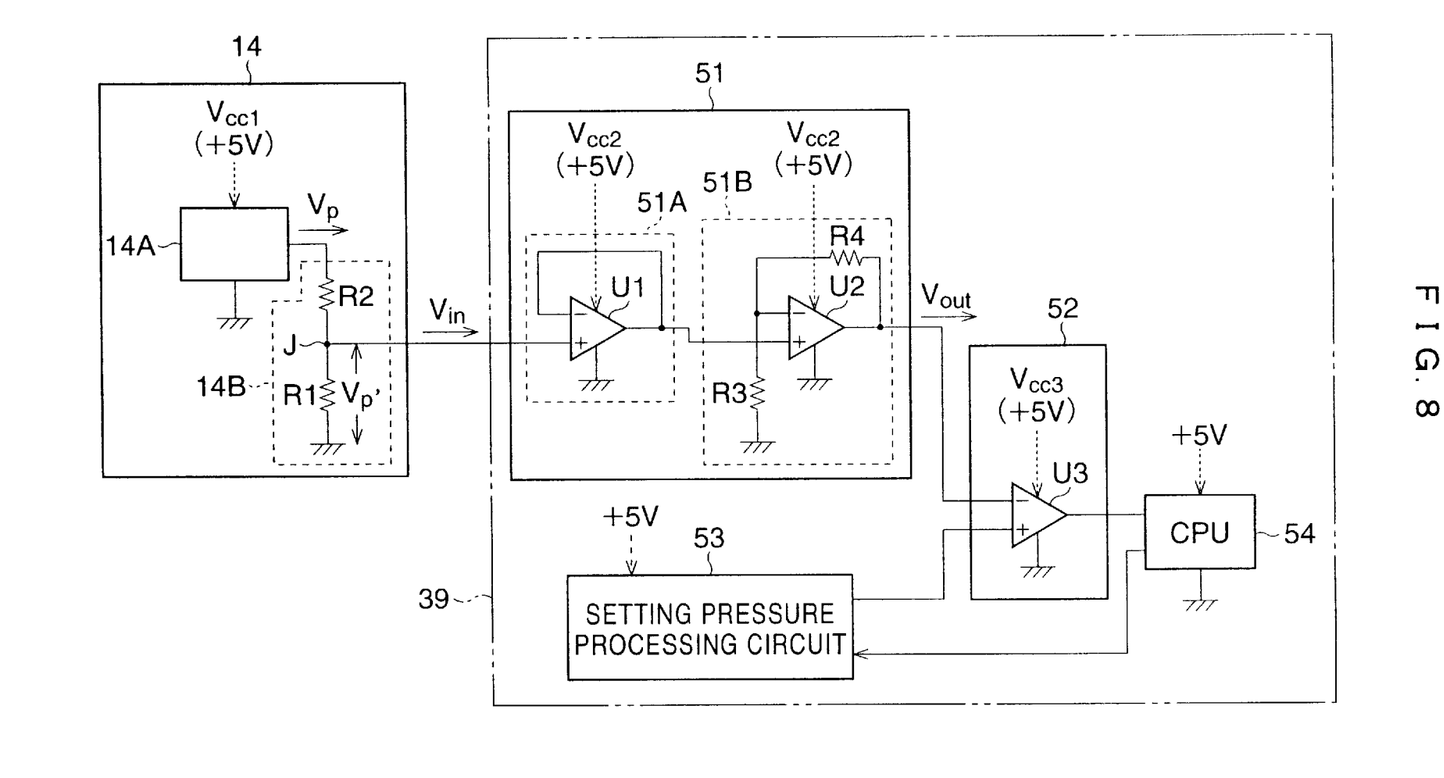
FIG. 8 is a view partially showing an electric circuit.

FIG. 8 is a view showing an electric circuit pertaining to the pressure-sensor 14 and system control circuit 39.

In the pressure-sensor 14, a sensor device 14A for outputting the pressure-voltage $V_p$ and a voltage descent processor 14B for lowering the pressure-voltage $V_p$ are provided. The voltage descent processor 14B is composed of a division resistance R1 and a division resistance R2. The resistance R1 is connected to an earth. In this embodiment, a resistance ratio, namely, a ratio of the resistance R1 to the resistance R2 is determined as follows:

$$R1:R2=1:1 \tag{7}$$

The pressure-voltage $V_p$ is divided into a voltage across the resistance R1 and a voltage across the resistance R2. Then, a voltage $V_p'$, which is a voltage at a node J, namely, the voltage across the resistance R1, is fed to the amplifier 51 as the input-voltage $V_{in}$. The voltage $V_p$ at the node J is given by:

$$V_p'=V_p \times R1/(R1+R2) \tag{8}$$

Herein, "R1/(R1+R2)" is denoted by a division ratio A. Using Equation (7), the division ratio A is as follows:

$$A = R1/(R1+R2) = 1/(R1/R1+R2/R1) \tag{9}$$
$$= 1/2$$

Therefore, in this embodiment, the voltage $V_p'$ is given by:

$$V_p'=1/2 \times V_p \tag{10}$$

As shown in Equations (8) and (10), the division ratio indicates a descent proportion of the pressure-voltage $V_p$.

The pressure-voltage $V_p$ is lowered, in short, divided by the voltage descent processor 14B such that the input-voltage $V_{in}$ ($V_p'$) is below the linear range of the input-voltage $V_{in}$. For example, when the pressure-voltage $V_p$ of 5.0 Volt, equaling the power-supply voltage $V_{cc1}$, is output from the sensor device 14A, the voltage $V_p'$ of 2.5 Volt is input to the amplifier 51. The pressure-voltage $V_p$ of 5.0 Volt is a maximum voltage in the range of output range of the pressure-voltage $V_p$, while the limitation input-voltage $V_k$ is 2.67 Volt as shown in Equation (6). Therefore, the range of the pressure-voltage $V_p$ does not exceed the linear range of the input-voltage $V_{in}$.

The amplifier 51 comprises a voltage-follower 51A and a noninverting amplifier 51B. The voltage-follower 51A for stabilizing a value of the input-voltage $V_{in}$ and output-voltage $V_{out}$ has an operational amplifier (op-amp) U1. On the other hand, the noninverting amplifier 51B for amplifying the input-voltage $V_{in}$ has an op-amp U2 and resistances R3 and R4. In the comparator 52, an op-amp U3 is provided. Note that, a voltage-gain (=1+R4/R3) of the noninverting amplifier 51B is the voltage-gain N (=1.5) of the amplifier 51. Further, the power-supply voltage $V_{cc1}$ of the pressure-sensor device 14A, the power-supply voltage $V_{cc2}$ of the amplifier (the op-amps U1 and U2) 51 and the power-supply voltage $V_{cc3}$ of the pressure-comparator (the op-amp U3) 52 are all 5.0 Volt.

When the input-voltage $V_{in}$ (the voltage $V_p'$) is 2.5 Volt, the output-voltage $V_{out}$ is as follows:

$$V_{out}=V_{in} \times N=2.5 \times 1.5=3.75 \tag{11}$$

The output-voltage $V_{out}$ (=3.75 Volt) is less than the maximum output-voltage $V_{max}$ (=4.0 Volt).

The output-voltage $V_{out}$ is fed to the comparator 52, whereby the output-voltage $V_{out}$ is compared with a setting pressure voltage output from the setting pressure processing circuit 53. Then, a voltage corresponding to a difference between the setting pressure voltage and the output-voltage $V_{out}$ is fed to the CPU 54.

Figure 9:
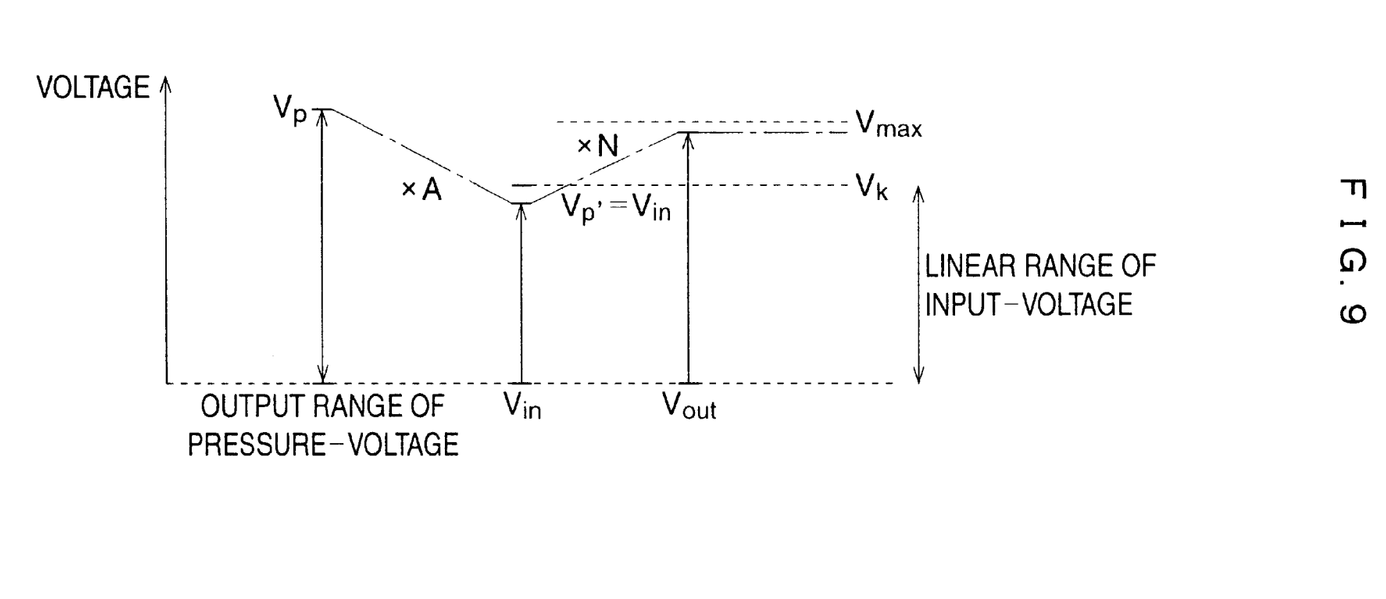
FIG. 9 is a view showing a relationship between a pressure-voltage, the input-voltage and the output-voltage of the amplifier.

FIG. 9 is a view showing a linear relationship of the pressure-voltage $V_p$ and the output-voltage $V_{out}$.

To maintain the linear relationship between the input-voltage $V_{in}$ and the output-voltage $V_{out}$, the division ratio A should be determined such that following formula is held for all pressure-value $V_p$:

$$V_p \times A \leq V_k = V_{max}/N \therefore A \leq V_{max}/(V_p \times N) \tag{12}$$

Note that, the voltage-gain N is predetermined to a value. Then, the resistance ratio (R1:R2) is determined in accordance with the division ratio A.

When the division ratio A is determined such that the formula (12) is held, the linear relationship between the input-voltage $V_{in}$ and the output-voltage $V_{out}$ is maintained. The input-voltage $V_{in}$ (the voltage $V_p'$) has obviously a linear relationship to the pressure-voltage $V_p$, as shown in Equation (10). Therefore, pressure-voltage $V_p$ has a linear relationship to the output-voltage $V_{out}$. Thus, the pressure value in the closed-space is measured precisely.

For example, when the power-supply voltage $V_{cc2}$ is 5.0 Volt, the maximum output-voltage $V_{max}$ is 4.0 Volt, and the output range of the pressure-voltage $V_p$ is from 0 to 5.0 Volt when the power-supply voltage $V_{cc1}$ is 5.0 Volt. Therefore, when the voltage-gain N is 1.5, the division ratio A should be determined such that the following formula is held:

$$V_{max}/(V_p \times N) = 4.0/(V_p \times 1.5) \tag{13}$$
$$\geq 4.0/(5.0 \times 1.5)$$
$$= 0.53 \geq A$$

As described above, in this embodiment, the voltage descent processor, composed of the resistances R1 and R2, is provided in the pressure-sensor 14. Thus, the pressure-voltage $V_p$ is divided, so that the pressure-voltage $V_p$ is lowered and then the voltage $V_p'$ is input to the amplifier 51 as for the input-voltage $V_{in}$. A magnitude of the division ratio A is determined such that the formula (12) is held, namely, the linear relationship between the pressure-voltage $V_p$ and the output-voltage $V_{out}$ is maintained. Thus, the pressure value in the closed-space can be measured precisely without changing the power-supply voltage $V_{cc2}$ to a larger voltage value, and further the output range of the pressure-voltage $V_p$ can be utilized effectively.

As the power-supply voltages $V_{cc1}$, $V_{cc2}$ and $V_{cc3}$ are all of equal voltage value, the electric power can be supplied to the pressure-sensor 14, the amplifier 51, and the comparator 52 via only converter 71. Namely, plural converters are not needed. Thus, the operation of the electric circuit can maintain stability without using a diode for protecting against an over-voltage in the circuit. Further, the total number of the components in the electric circuit can be decreased.

In a modification, the voltage-descent processor 14B may be provided in the system control circuit 39 in place of the pressure-sensor 14.

Further, the resistance ratio (R1:R2) may be changed on condition that the formula (12) is held.

Finally, it will be understood by those skilled in the art that the foregoing description is of preferred embodiment of the device, and that various changes and modifications may be made to the present invention without departing from the spirit and scope thereof.

The present disclosure relates to subject matters contained in Japanese Patent Application No.10-352626 (filed on Dec. 11, 1998) which is expressly incorporated herein, by reference, in its entirety.

What is claimed is:

1. An air delivery unit for an endoscope having a closed-space, a pressure in said closed-space being adjusted by measuring the pressure and selectively discharging air in said closed-space, said air delivery unit comprising:

a pressure-sensor that outputs a detection pressure-voltage that corresponds to a value of said pressure in said closed-space;

a voltage lowering processor that receives the output of the pressure sensor and outputs a lowered pressure-voltage obtained by lowering said detection pressure-voltage;

an amplifier that receives the output of the voltage lowering processor and outputs an amplified pressure-voltage obtained by amplifying said lowered pressure-voltage; and an electric power supplier that applies a power-supply voltage to said pressure-sensor and to said amplifier, said voltage lowering processor lowering said detection pressure-voltage to be in a linear range of said amplifier, said amplified pressure-voltage having a linear relationship to said lowered pressure-voltage.

2. The air delivery unit for the endoscope of claim 1, wherein a power-supply voltage of said pressure-sensor equals that of said amplifier.

3. The air delivery unit for the endoscope of claim 2, further comprising a comparator that compares said amplified pressure-voltage output from said amplifier to a setting pressure voltage corresponding to a setting pressure set by an operator, said electric power supplier applying a power-supply voltage, equaling that of said pressure-sensor and that of said amplifier, to said comparator.

4. The air delivery unit for the endoscope of claim 2, said voltage lowering processor comprises at least one resistance for dividing said detection pressure-voltage, whereby said detection pressure-voltage is lowered.

5. The air delivery unit for the endoscope of claim 4, said voltage lowering processor comprises two resistances, a voltage across one resistance of said two resistances, connected to an earth, being fed to said amplifier as said lowered pressure-voltage.

6. The air delivery of claim 4, wherein a division ratio of said resistances, corresponding to a lowering proportion of said detection pressure-voltage, is determined such that said lowered pressure-voltage obtained by dividing said detection pressure-voltage in accordance with said division ratio does not exceed a limitation input-voltage that represents a maximum voltage in which the linear relationship can be maintained.

7. The air delivery unit for the endoscope of claim 2, wherein a maximum voltage in a range of said detection pressure-voltage output from said pressure-sensor is equal to said power-supply voltage of said pressure-sensor.

8. The air delivery unit of claim 1, wherein said amplifier comprises a voltage-follower that stabilizes said lowered pressure-voltage and said amplified pressure-voltage, and a non-inverting amplifier that amplifies said lowered pressure-voltage by a predetermined voltage-gain amount.

9. An air delivery unit for an endoscope having a closed-space, a pressure in said closed-space being adjusted by measuring the pressure and selectively discharging air in said closed-space, said air delivery unit comprising:

a pressure-sensor that outputs a detection pressure-voltage that corresponds to a value of said pressure in said closed-space;

a voltage lowering processor that outputs a lowered pressure-voltage obtained by lowering said detection pressure-voltage;

an amplifier that outputs an amplified pressure-voltage obtained by amplifying said lowered pressure-voltage;

an electric power supplier that applies a power-supply voltage to said pressure-sensor and to said amplifier, said voltage lowering processor lowering said detection pressure-voltage such that said lowered pressure-voltage is in a linear range of said amplifier, so that said amplified pressure-voltage has a linear relationship to said lowered pressure-voltage; and a comparator that compares said amplified pressure-voltage output from said amplifier to a setting pressure voltage corresponding to a setting pressure set by an operator, said electric power supplier applying a power-supply voltage, equaling that of said pressure-sensor and that of said amplifier, to said comparator.

* * * * *